(12) United States Patent
Nakaoka et al.

(10) Patent No.: US 6,897,351 B2
(45) Date of Patent: May 24, 2005

(54) DISPOSABLE DIAPER WITH PORTION ON SKIN-SIDE SHEET TO PREVENT PASSAGE OF URINE OR OTHER BODILY WASTE

(75) Inventors: Kenji Nakaoka, Tokushima (JP); Masaru Fujioka, Tokushima (JP); Satoshi Maeda, Tokushima (JP); Kazuyo Mori, Tokushima (JP)

(73) Assignee: Toyo Eizai Kabushiki Kaisha, Ehime (JP)

( * ) Notice: Subject to any disclaimer, the term of this patent is extended or adjusted under 35 U.S.C. 154(b) by 126 days.

(21) Appl. No.: 09/890,881

(22) PCT Filed: Nov. 30, 2000

(86) PCT No.: PCT/JP00/08484

§ 371 (c)(1),
(2), (4) Date: Jul. 30, 2001

(87) PCT Pub. No.: WO01/39713

PCT Pub. Date: Jun. 7, 2001

(65) Prior Publication Data

US 2002/0138061 A1 Sep. 26, 2002

(30) Foreign Application Priority Data

Dec. 1, 1999 (JP) .............................. 11-342349

(51) Int. Cl.$^7$ ............................ A61F 13/15; A61F 13/20
(52) U.S. Cl. .................................. 604/381; 604/385.01
(58) Field of Search ................ 604/385.01, 385.24, 604/385.25, 385.26, 385.27, 385.28, 381

(56) References Cited

U.S. PATENT DOCUMENTS

| | | | | |
|---|---|---|---|---|
| 4,842,666 A | * | 6/1989 | Werenicz | 156/161 |
| 5,582,606 A | * | 12/1996 | Bruemmer et al. | 604/373 |
| 5,624,426 A | * | 4/1997 | Roe et al. | 604/385.28 |
| 5,662,637 A | * | 9/1997 | Kitaoka et al. | 604/385.28 |
| 5,672,166 A | * | 9/1997 | Vandemoortele | 156/164 |
| 5,718,698 A | * | 2/1998 | Dobrin et al. | 604/383 |
| 6,068,620 A | * | 5/2000 | Chmielewski | 604/358 |
| 6,123,694 A | * | 9/2000 | Pieniak et al. | 604/385.01 |
| 6,159,190 A | * | 12/2000 | Tanaka et al. | 604/385.24 |
| 6,248,097 B1 | * | 6/2001 | Beitz et al. | 604/358 |
| 6,270,487 B1 | * | 8/2001 | Sheehan et al. | 604/385.01 |
| 6,371,950 B1 | * | 4/2002 | Roslansky et al. | 604/385.01 |

* cited by examiner

Primary Examiner—Larry I. Schwartz
Assistant Examiner—Michele Kidwell
(74) Attorney, Agent, or Firm—Jordan and Hamburg LLP

(57) ABSTRACT

In a disposable diaper in which an absorbent body is provided between a water-repellent outer sheet and a hydrophilic skin-side sheet made of a nonwoven fabric, raisable strips made of a nonwoven fabric are provided at the opposite sides of the skin-side sheet, elastic threads for raisable gathers are provided in inner edge portions of the raisable strips and the outer edge portions of the raisable strips are adhered to the skin-side sheet, an ooze preventing portion for preventing an ooze of urine and other bodily waste is formed at opposite end portions of the skin-side sheet. Therefore, even if urine and other bodily waste permeate into the skin-side sheet, they do not ooze out from the end portion of the skin-side sheet.

26 Claims, 4 Drawing Sheets

DISPOSABLE DIAPER WITH PORTION ON SKIN-SIDE SHEET TO PREVENT PASSAGE OF URINE OR OTHER BODILY WASTE

TECHNICAL FIELD

The present invention relates to a disposable diaper capable of effectively and inexpensively preventing urine and other bodily waste from oozing out from an end portion of a skin-side sheet.

BACKGROUND ART

A known disposable diaper is such that an absorbent body is provided between an water-repellent outer sheet and a hydrophilic skin-side sheet made of a nonwoven fabric, water-repellent raisable strips are provided at the opposite sides of the skin-side sheet, elastic threads for raisable gathers are provided at inner edge portions of the raisable strips and outer edge portions of the raisable strips are adhered to the skin-side sheet.

In the above disposable diaper, a lateral leak of urine and other bodily waste is prevented by the raised gathers formed by the elastic threads provided in the raisable strips.

However, since the skin-side sheet is hydrophilic, if urine and the like permeate into this skin-side sheet, there is a problem that they may ooze out from an end portion of the skin-side sheet to stain clothes.

In view of this, a disposable diaper has been proposed in which an end of the outer sheet is rolled up to wrap an end of the skin-side sheet and is adhered to the upper surface of the skin-side sheet, so that even if urine or other bodily waste oozes out from the end portion of the skin-side sheet, clothes are not stained by the presence of the rolled up outer sheet. However, this disposable diaper requires an operation step of rolling up the end portion of the outer sheet, leading to an increased production cost.

In view of the problem residing in the prior art, an object of the present invention is to provide a disposable diaper capable of effectively and inexpensively preventing urine and other bodily waste from oozing out from an end portion of a skin-side sheet.

DISCLOSURE OF THE INVENTION

The invention is directed to a disposable diaper in which an absorbent body is provided between a water-repellent outer sheet and a hydrophilic skin-side sheet made of a nonwoven fabric, raisable strips made of a nonwoven fabric are provided at the opposite sides of the skin-side sheet, elastic threads for raisable gathers are provided in inner edge portions thereof and the outer edge portions of the raisable strips are adhered to the skin-side sheet, wherein an ooze preventing portion for preventing an ooze of urine and other bodily waste is formed at an end portion of the skin-side sheet.

According to the invention, since the ooze preventing portion is formed at the end portion of the skin-side sheet, even if urine and other bodily waste permeate into the skin-side sheet, they do not ooze out from the end portion of the skin-side sheet.

BEST MODE FOR CARRYING OUT THE INVENTION

Figure 1:
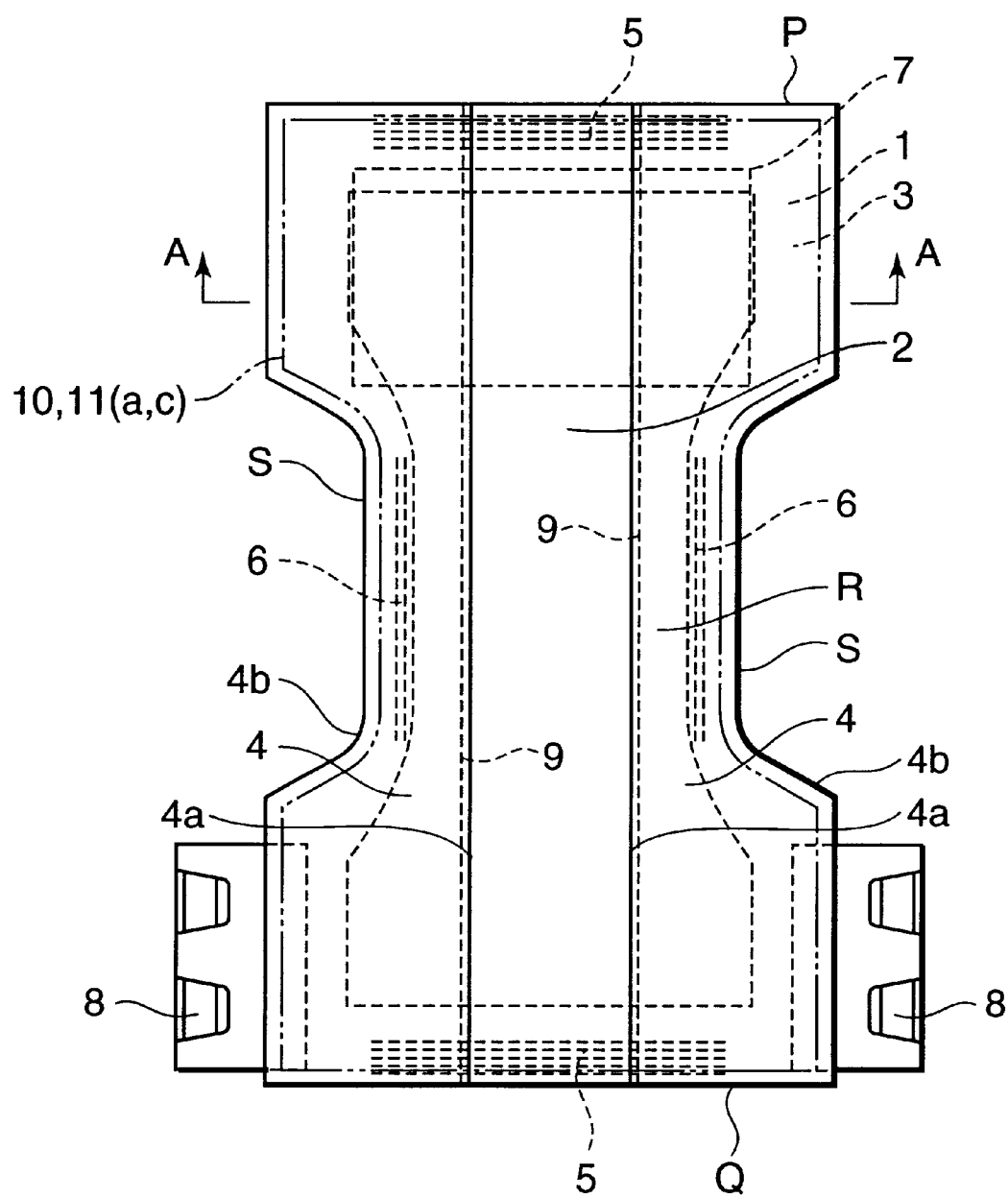
FIG. 1 is a front view of an inventive disposable diaper in its developed state.
Figure 3A:
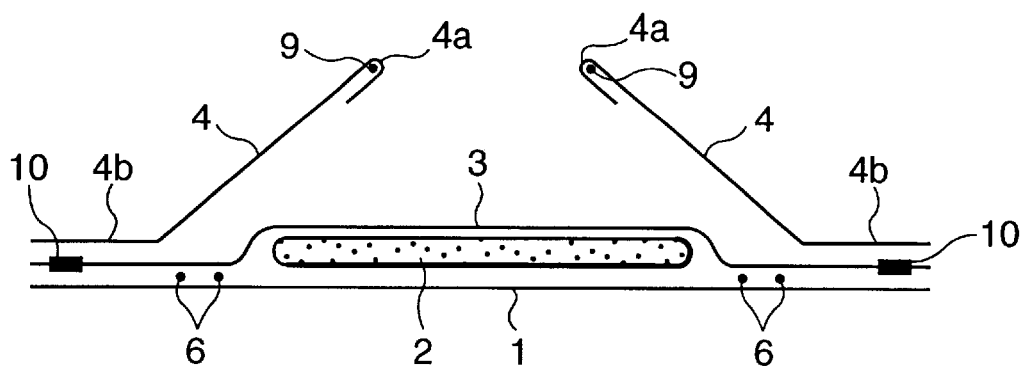
FIGS. 3A, 3B and 3C are schematic sections along A—A of FIG. 1, respectively.
Figure 3B:
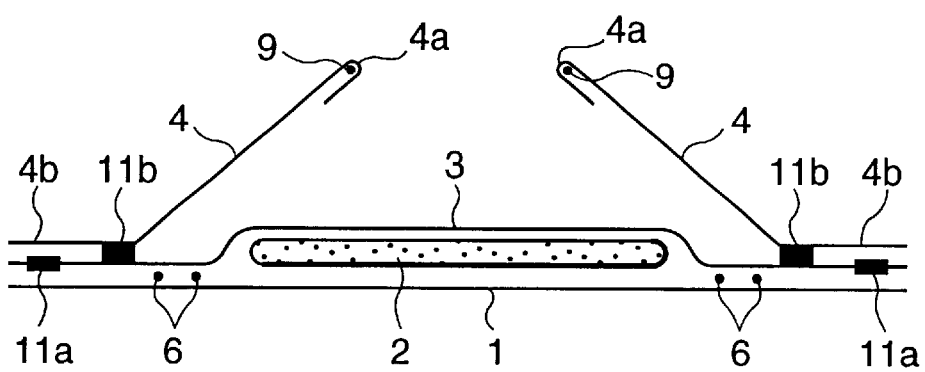
Figure 3C:
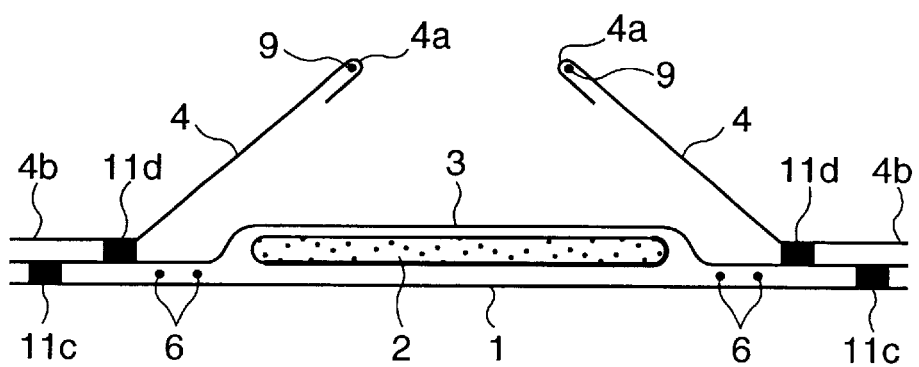
Figure 4:
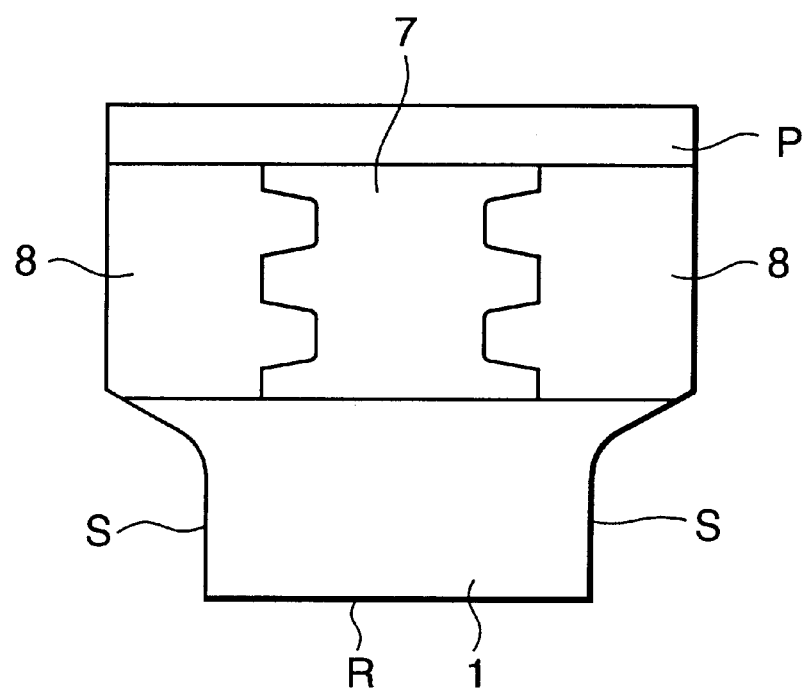
FIG. 4 is a front view of the disposable diaper in its used state.

Hereinafter, one embodiment of the present invention is described in detail with reference to the accompanying drawings. FIG. 1 is a front view of an inventive disposable diaper in its developed state, FIG. 2 is an exploded perspective view of the disposable diaper, FIGS. 3A, 3B and 3C are schematic sections along A—A of FIG. 1, respectively, and FIG. 4 is a front view of the disposable diaper in its used state.

Figure 2:
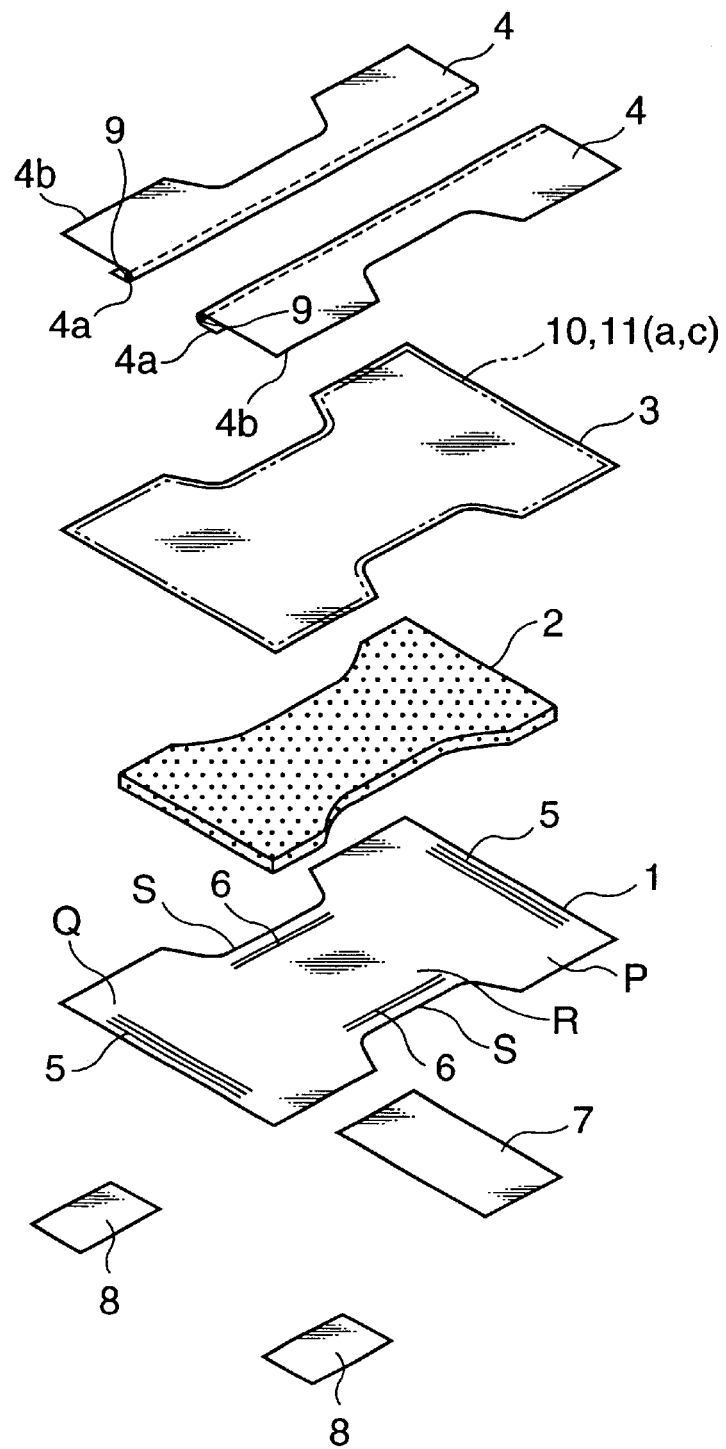
FIG. 2 is an exploded perspective view of the disposable diaper.

As shown in FIG. 2, the disposable diaper is basically comprised of an outer sheet 1, an absorbent body 2, a skin-side sheet 3, and a pair of left and right raisable strips 4.

The outer sheet 1 is formed of a nonwoven fabric made of synthetic resin fibers having water repellency or a synthetic resin film, and leg openings S are formed at the opposite sides of a crotch portion R between a front part P and a rear part Q.

A plurality of elastic threads 5 for waist gathers are provided on the upper surfaces of the front and rear parts P, Q of the outer sheet 1 while being stretched in widthwise direction, and a plurality of elastic threads 6 for leg gathers are provided on the upper surfaces of the opposite leg openings S while being stretched in lengthwise direction.

Further, a frontal tape 7 is attached to the lower surface of the front part P of the outer sheet 1, and fastening tapes 8 are respectively attached to the opposite sides of the rear part Q between the outer sheet 1 and the skin-side sheet 3 or between the outer sheet 1 and the raisable strips 4 so as to assemble the disposable diaper in a 3D manner by being adhered to the frontal tape 7 as shown in FIG. 4 when the disposable diaper is used.

The absorbent body 2 is formed of a mixture of natural pulp fibers, synthetic resin fibers and a high water-absorbent polymer material or by laminating these materials, and is a flat member which is about one size smaller than the outer sheet 1, substantially in the form of a rectangle and wrapped in a tissue paper. This absorbent body 2 is adhered to the upper surface of the outer sheet 1.

The skin-side sheet 3 is formed of a hydrophilic nonwoven fabric made of synthetic resin fibers and has the same outer configuration as the outer sheet 1. The lower surface of the skin-side sheet 3 and the upper surface of the outer sheet 1 are substantially entirely adhered to each other with the absorbent body 2 and the elastic threads 5, 6 provided therebetween. The skin-side sheet 3 may have a rectangular shape having a width equal to a spacing between the leg openings S.

The left and right raisable strips 4 are formed of a nonwoven fabric made of synthetic resin fibers having water repellency, have substantially the same length as the outer sheet 1 and the skin-side sheet 3, and are formed at portions corresponding to the leg openings S with leg openings having the same shape.

The respective raisable strips 4 have their inner edge portions 4a folded downwardly and inwardly. The inner edge portions 4a cover the opposite sides of the upper surface of the absorbent body 2 and the lower surfaces of outer edge portions 4b are adhered to the upper surface of the skin-side sheet 3.

Elastic threads 9 for raisable gathers are provided in the inner edge portions 4a of the respective raisable strips 4 while being stretched substantially over the entire length of the raisable strips 4.

The respective elastic threads 5, 6, 9 are made of strip-shaped or thread-shaped natural rubber or synthetic rubber, and the waist gathers, raisable gathers and leg gathers are naturally formed by the shrinking forces of the elastic threads 5, 6, 9.

The most significant feature of the present invention is that an ooze preventing portion for preventing an ooze of urine and the like is provided at opposite end portions of the hydrophilic skin-side sheet 3. One example of the ooze preventing portion is a water repelled portion 10 formed by applying an adhesive such as a hot melt adhesive to the end portion of the skin-side sheet 3 and causing the adhesive to permeate into clearances between fibers of the nonwoven fabric as shown in FIG. 3A. In the case of such a construction, the skin-side sheet may not be a nonwoven fabric made of thermoplastic resin fibers.

Alternatively, as shown in FIG. 3B, a treatment may be given to prevent an ooze of urine and the like by heat-sealing the end portion of the skin-side sheet 3 to fill up clearances between the fibers of the nonwoven fabric, thereby forming a first film portion 11a. In the case of such a construction, a nonwoven fabric made of thermoplastic resin fibers is used for the skin-side sheet 3 since the fibers of the skin-side sheet 3 need to be melted and made into a film by the heat of heat-sealing. However, it is sufficient for the nonwoven fabric of the skin-side sheet 3 to possess such thermoplasticity as to be made into a film by heat-sealing, and not all the fibers forming the nonwoven fabric need to be thermoplastic resin fibers, i.e. fibers having no thermoplasticity may be mixed. It should be noted that an ultrasonic fusing means may be adopted instead of heat-sealing.

Further as shown in FIG. 3C, the respective end portions of the skin-side sheet 3 and the outer sheet 1 are joined by heat-sealing, and a first film portion 11c may be formed by at least filling up clearances between the fibers of the nonwoven fabric of the skin-side sheet 3. Since the outer sheet 1 is made of a water-repellent material, the ooze preventing portions can be formed by making the skin-side sheet 3 into a film to lose water permeability. Regardless of whether the outer sheet 1 is a nonwoven fabric or a film, it is preferably made of a thermoplastic material as described above like the skin-side sheet 3. The heat-sealed portion can be made into a film merely by joining the sheets 1 and 3 by means of heat-sealing.

As shown in FIG. 3B, second film portions 11b may be formed by making the raisable strips 4 and the skin-side sheet 3 inwardly of the first film portions 11a into films while joining them by means of heat-sealing. Clearances between the fibers of the nonwoven fabrics of the raisable strips 4 and the skin-side sheet 3 are filled up and the raisable strips 4 and the skin-side sheet 3 are joined to form the film portions 11b. This construction is further effective in preventing the ooze of urine and the like since ooze prevention is performed at two stages.

Further, as shown in FIG. 3C, second film portions 11d may be formed by joining the raisable strips 4 and the skin-side sheet 3 inwardly of the first film portion 11c by means of heat-sealing. It should be noted that the first film portion may be formed by the skin-side sheet 3 and the raisable strips 4 and the second film portions may be formed by the skin-side sheet 3 and the outer sheet 1.

The water repelled portions 10 by the hot melt adhesive at the end portion of the skin-side sheet 3 and the film portions 11a, 11c formed by heat-sealing preferably extend over the entire outer periphery of the skin-side sheet 3 as shown in chain double-dashed line in FIGS. 1 and 2 in view of ooze prevention of urine and other bodily waste.

In the disposable diaper constructed as above, the water repelled portions 10 and the film portions 11a, 11c for the ooze preventing treatment of urine and the like are formed at the end portion of the hydrophilic skin-side sheet 3. Accordingly, even if urine or the like permeates into the skin-side sheet 3, there is no danger of staining the clothes since the permeated urine and the like do not ooze out from the end portion of the skin-side sheet 3.

Further, since it is not necessary, unlike the prior art, to roll up the end portion of the outer sheet 1 to wrap the end portion of the skin-side sheet 3, an operation step of rolling up the end of the outer sheet 1 no longer necessary, contributing to a decrease in production cost.

Furthermore, since the outer edges of the outer sheet 1, the skin-side sheet 3 and the raisable strips 4 can be aligned, displacements thereof when they are placed one over another during manufacturing can be prevented.

If the second film portions 11b or 11d is formed by joining the raisable strips 4 and the skin-side sheet 3 by means of heat-sealing, urine and other bodily waste permeated into the skin-side sheet 3 do not ooze out beyond the film portions 11b, 11d. Therefore, an ooze of urine and the like can be more effectively prevented.

Although the invention is applied to the disposable diaper in the foregoing embodiment, it is, of course, also applicable to such disposable underpants that the first absorbent body is mounted on the skin-side sheet placed on the outer sheet.

INDUSTRIAL APPLICABILITY

As described above, the inventive disposable diaper is useful as disposable diapers or disposable underpants which can effectively and inexpensively prevent an ooze of urine and bodily waste from the end portion of the skin-side sheet.

What is claimed is:

1. A disposable diaper, comprising:

a water-repellent sheet;

a skin-side sheet joined with said water-repellant sheet;

an absorbent body disposed between the water-repellent sheet and the skin-side sheet; and said skin-side sheet being comprised of fibers arranged as a nonwoven fabric having clearances between the fibers, said skin side sheet including a hydrophilic region and an ooze preventing portion extending at least partially along opposite sides of said skin-side sheet, said ooze preventing portion separating said hydrophilic region from a peripheral edge of said skin-side sheet over an extent of said ooze preventing portion, said ooze preventing portion of said skin-side sheet being rendered impermeable to a passage of water from said hydrophilic region to said peripheral edge by permeation of an adhesive into the clearances between the fibers whereby migration of bodily waste from said hydrophilic region to said peripheral edge across said ooze preventing portion is prevented.

2. A disposable diaper according to claim 1, further comprising raisable strips made of a nonwoven fabric and including edge portions adhered to the skin-side sheet at said opposite sides of the skin-side sheet.

3. A disposable diaper according to claim 2, wherein:

said water-repellent sheet and said skin-side sheet have approximately a same outer configuration; and said peripheral edge of said skin-side sheet and respective peripheral edges of said water-repellent sheet and said raisable strips are in mutual alignment.

4. A disposable diaper according to claim 1, wherein said ooze preventing portion extends continuously over substantially an entire outer periphery of the skin-side sheet.

5. A disposable diaper according to claim 1, wherein adhesive is a hot melt adhesive.

6. A disposable diaper according to claim 1, wherein said skin-side sheet includes a second ooze preventing portion located adjacent to said ooze preventing portion, said second ooze preventing portion of said skin-side sheet being water-impermeable thereby preventing migration of bodily waste thereacross.

7. A disposable diaper, comprising:
a water-repellent sheet;
an absorbent body; and
a skin-side sheet formed of a nonwoven fabric comprised of fibers having clearances therebetween, said skin-side sheet being joined to said water-repellant sheet with said absorbent body interposed therebetween, said skin-side sheet including a hydrophilic region and an ooze preventing portion extending at least partially along opposite sides of said skin-side sheet, said ooze preventing portion separating said hydrophilic region from a peripheral edge of said skin-side sheet over an extent of said ooze preventing portion, said ooze preventing portion being formed as a film by a filling up of the clearances between the fibers of said nonwoven fabric, thereby rendering the hydrophilic skin-side sheet water-impermeable within said ooze preventing portion to prevent migration of bodily waste thereacross from said hydrophilic region to said peripheral edge.

8. A disposable diaper according to claim 7, further comprising raisable strips made of a nonwoven fabric and including edge portions adhered to the skin-side sheet at said opposite sides of the skin-side sheet.

9. A disposable diaper according to claim 7, wherein said ooze preventing portion extends continuously over substantially an entire outer periphery of the skin-side sheet.

10. A disposable diaper, comprising:
a water-repellent sheet;
an absorbent body; and
a hydrophilic skin-side sheet formed of a nonwoven fabric comprised of fibers having clearances therebetween, said hydrophilic skin-side sheet being joined to said water-repellant sheet with said absorbent body interposed therebetween, said hydrophilic skin-side sheet including an ooze preventing portion formed inward of a peripheral edge and extending at least partially along opposite sides of said hydrophilic skin-side sheet by heat-sealing a region inwardly adjacent to the peripheral edge of the skin-side sheet to fill up the clearances between fibers of the nonwoven fabric, thereby rendering the hydrophilic skin-side sheet water-impermeable within said ooze preventing portion to prevent migration of bodily waste thereacross from a region of said hydrophilic skin-side sheet inward of said ooze preventing portion to said peripheral edge.

11. A disposable diaper according to claim 10, further comprising raisable strips made of a nonwoven fabric and including edge portions adhered to the skin-side sheet at said opposite sides of the skin-side sheet.

12. A disposable diaper according to claim 11, wherein said ooze preventing portion extends continuously over substantially an entire outer periphery of the skin-side sheet.

13. A disposable diaper according to claim 11, wherein:
said raisable strips include a thermoplastic material; and
said hydrophilic skin-side sheet includes a second ooze preventing portion located adjacent to said ooze preventing portion, said second ooze preventing portion being formed by heat sealing the edge portions of said raisable strips to the hydrophilic skin-side sheet adjacent to said ooze preventing portion to concomitantly join the raisable strips with the hydrophilic skin-side sheet and form said skin-side sheet into a film in which the clearances between the fibers are filled up over a joined region corresponding to said second ooze preventing portion.

14. A disposable diaper, comprising:
a water-repellent sheet formed of one of a film and a nonwoven fabric, each which comprises a thermoplastic material;
an absorbent body; and
a hydrophilic skin-side sheet formed of a nonwoven fabric comprised of fibers having clearances therebetween, at least a portion of said fibers including thermoplastic resin fibers, said hydrophilic skin-side sheet being joined to said water-repellent sheet with said absorbent body interposed therebetween, said hydrophilic skin-side sheet including an ooze preventing portion which is a film portion formed by joining said hydrophilic skin-side sheet to said water-repellent sheet by heat-sealing which concomitantly forms said hydrophilic skin-side sheet into a film in which the clearances between the fibers are filled up over a joined region corresponding to said ooze preventing portion which extends at least partially along opposite sides of said hydrophilic skin-side sheet.

15. A disposable diaper according to claim 14, further comprising raisable strips made of a nonwoven fabric and including edge portions adhered to the skin-side sheet at said opposite sides of the skin-side sheet.

16. A disposable diaper according to claim 14, wherein said ooze preventing portion extends continuously over substantially an entire outer periphery of the skin-side sheet.

17. A disposable diaper according to claim 15, wherein:
said raisable strips include a thermoplastic material; and
said hydrophilic skin-side sheet includes a second ooze preventing portion located adjacent to said ooze preventing portion, said second ooze preventing portion of said skin-side sheet having a material property which lacks water permeability thereby preventing migration of bodily waste thereacross, said second ooze preventing portion being formed by heat sealing the edge portions of said raisable strips to the hydrophilic skin-side sheet adjacent to said ooze preventing portion to concomitantly join the raisable strips with the hydrophilic skin-side sheet and form said skin-side sheet into a film in which the clearances between the fibers are filled up over a joined region corresponding to said second ooze preventing portion.

18. A method of making a disposable diaper, comprising:
interposing an absorbent body between a water-repellent sheet and a hydrophilic skin-side sheet, said hydrophilic skin-side sheet being formed of a nonwoven fabric comprised of fibers having clearances therebetween, at least a portion of said fibers including thermoplastic resin fibers;
joining said water-repellent sheet to said hydrophilic skin-side sheet; and
forming an ooze preventing portion extending at least partially along opposite sides inward of a peripheral edge of said hydrophilic skin-side sheet by treating said hydrophilic skin-side sheet to fill up the clearances between the fibers thereof, thereby forming a film portion which is water-impermeable to passage of water across said ooze preventing portion from a region of said hydrophilic skin-side sheet inward of said ooze preventing portion to said peripheral edge.

19. A method according to claim 18, further comprising adhering raisable strips made of a nonwoven fabric having outer edge portions to the hydrophilic skin-side sheet.

20. A method according to claim 19, wherein:

said raisable strips are made of a nonwoven fabric including a thermoplastic material; and said step of adhering includes heat sealing outer edge portions of said raisable strips to the hydrophilic skin-side sheet adjacent to said ooze preventing portion to concomitantly join the raisable strips with the hydrophilic skin-side sheet and form said skin-side sheet into a film over a joined region corresponding to a second ooze preventing portion located adjacent to said ooze preventing portion.

21. A method according to claim 18, wherein said step of treating in said step of forming includes heat-sealing said skin-side sheet into the film portion.

22. A method according to claim 18, wherein said step of treating in said step of forming includes ultrasonically fusing said skin-side sheet into the film portion.

23. A method according to claim 18, wherein:

said water-repellent sheet is one of a film and a nonwoven fabric each which comprises a thermoplastic material; and said step of treating in said step of forming, and said step of joining said hydrophilic skin-side sheet to said water-repellent sheet, are accomplished in a shared step including heat-sealing which, in addition to joining the hydrophilic skin-side sheet to said water-repellent sheet, concomitantly forms said skin-side sheet into the film portion over a joined region of said hydrophilic skin-side sheet to said water-repellent sheet corresponding to said ooze preventing portion.

24. A method according to claim 23, further comprising adhering raisable strips made of a nonwoven fabric including a thermoplastic material by heat sealing outer edge portions thereof to the hydrophilic skin-side sheet adjacent to said joined region to concomitantly join the raisable strips with the hydrophilic skin-side sheet and form said skin-side sheet into a film over a second joined region corresponding to a second ooze preventing portion located adjacent to said ooze preventing portion.

25. A method of making a disposable diaper, comprising:

interposing an absorbent body between a water-repellent sheet and a hydrophilic skin-side sheet, said hydrophilic skin-side sheet being formed of a nonwoven fabric comprised of fibers having clearances therebetween;

joining said water-repellent sheet to said hydrophilic skin-side sheet; and forming an ooze preventing portion extending at least partially along opposite sides inward of a peripheral edge of said hydrophilic skin-side sheet by applying an adhesive to the skin-side sheet and causing the adhesive to permeate into the clearances between the fibers thereby rendering the nonwoven fabric water-impermeable within said ooze preventing portion to prevent migration of bodily waste across said ooze preventing portion from a portion of said skin-side sheet inward of said ooze preventing portion to said peripheral edge.

26. A disposable diaper according to claim 25, wherein: said adhesive is a hot melt adhesive.

* * * * *